United States Patent
Wang et al.

(10) Patent No.: US 11,280,015 B2
(45) Date of Patent: Mar. 22, 2022

(54) NON-ENZYME SENSOR, NON-ENZYME SENSOR ELEMENT AND FABRICATING METHOD THEREOF

(71) Applicant: NATIONAL TSING HUA UNIVERSITY, Hsinchu (TW)

(72) Inventors: Hsiang-Yu Wang, Hsinchu (TW); Yi-Yu Chen, Taoyuan (TW); Shih-Hao Lin, New Taipei (TW); Yu-Sheng Lin, Kaohsiung (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 0 days.

(21) Appl. No.: 17/153,861

(22) Filed: Jan. 20, 2021

(65) Prior Publication Data
US 2021/0223198 A1    Jul. 22, 2021

(30) Foreign Application Priority Data

Jan. 21, 2020  (TW) ............................. 109102297

(51) Int. Cl.
| | |
|---|---|
| *C25D 5/48* | (2006.01) |
| *C25D 7/00* | (2006.01) |
| *C25D 5/54* | (2006.01) |
| *C25D 5/18* | (2006.01) |
| *C25D 3/12* | (2006.01) |
| *G01N 27/30* | (2006.01) |

(52) U.S. Cl.
CPC ............... *C25D 5/48* (2013.01); *C25D 3/12* (2013.01); *C25D 5/18* (2013.01); *C25D 5/54* (2013.01); *C25D 7/00* (2013.01); *G01N 27/308* (2013.01)

(58) Field of Classification Search
CPC ............... C25D 5/18; C25D 5/48; C25D 9/08
See application file for complete search history.

(56) References Cited

U.S. PATENT DOCUMENTS

| | | | | |
|---|---|---|---|---|
| 4,384,928 A | * | 5/1983 | Hall | C25D 9/08 205/188 |
| 5,326,454 A | * | 7/1994 | Engelhaupt | C25D 5/605 205/67 |
| 8,551,317 B2 | * | 10/2013 | Kurokawa | C23C 8/40 205/320 |

(Continued)

OTHER PUBLICATIONS

Sungjin Kim et al., "Non-enzymatic electrochemical lactate sensing by NiO and Ni(OH)2 electrodes: A mechanistic investigation", Electrochimica Acta, published on Apr. 25, 2018, vol. 276, pp. 240-246, published by Elsevier Ltd., Netherlands.

(Continued)

*Primary Examiner* — Brian W Cohen
(74) *Attorney, Agent, or Firm* — CKC & Partners Co., LLC

(57) ABSTRACT

A fabricating method of a non-enzyme sensor element includes a printing step, a coating step and an electroplating step. In the printing step, a conductive material is printed on a surface of a substrate to form a working electrode, a reference electrode and an auxiliary electrode, and a porous carbon material is printed on the working electrode to form a porous carbon layer. In the coating step, a graphene film material is coated on the porous carbon layer of the working electrode to form a graphene layer. In the electroplating step, a metal is electroplated on the graphene layer by a pulse constant current to form a catalyst layer including a metal oxide.

5 Claims, 9 Drawing Sheets

(56) References Cited

U.S. PATENT DOCUMENTS

2019/0119822 A1\* 4/2019 Fontecave ............ C25B 11/077

OTHER PUBLICATIONS

D. A. Sakharov et al., "Relationship between Lactate Concentrations in Active Muscle Sweat and Whole Blood", Bulletin of Experimental Biology and Medicine, published on Nov. 25, 2010, vol. 150, No. 1, pp. 83-85, published by Springer Science+Business Media, Inc., Germany.

\* cited by examiner

NON-ENZYME SENSOR, NON-ENZYME SENSOR ELEMENT AND FABRICATING METHOD THEREOF

RELATED APPLICATIONS

This application claims priority to Taiwan Application Serial Number 109102297, filed Jan. 21, 2020, which is herein incorporated by reference.

BACKGROUND

Technical Field

The present disclosure relates to a sensor element and a fabricating method thereof. More particularly, the present disclosure relates to a non-enzyme sensor element and a fabricating method thereof.

Description of Related Art

In the field of clinical medicine, detecting the concentration of organic substances in the human body can be used to determine the signs of diseases and the state of the human body, and can be further applied in the fields of sports management and disease detection, etc.

Lactic acid is considered to be an important physiological index, but the conventional techniques for detecting lactic acid are very expensive, taking long time for detection, or sensitive to the environmental influence, which cannot satisfy the requirements for point-of-care medical detections or other fields. Furthermore, the conventional non-enzyme sensor detects the lactic acid in two ranges of 0.5 mM to 35 mM and 11.9 mM to 188 mM. However, the range of the lactic acid concentration in the human body fluid can be as wide as 0 mM to 60 mM. It shows that each conventional non-enzyme sensor alone is not suitable for human metabolites detection.

Therefore, it is important to develop a rapid and accurate non-enzyme sensor and accurate non-enzyme sensor element which is suitable for detecting human metabolites.

SUMMARY

According to one aspect of the present disclosure, a fabricating method of a non-enzyme sensor element includes a printing step, a coating step and an electroplating step. In the printing step, a conductive material is printed on a surface of a substrate to form a working electrode, a reference electrode and an auxiliary electrode, and a porous carbon material is printed on the working electrode to form a porous carbon layer. In the coating step, a graphene film material is coated on the porous carbon layer of the working electrode to form a graphene layer. In the electroplating step, a metal is electroplated on the graphene layer by a pulse constant current to form a catalyst layer including a metal oxide.

According to another aspect of the present disclosure, a non-enzyme sensor element fabricated by the fabricating method of the non-enzyme sensor element according to the aforementioned aspect and for detecting a concentration of an analyte includes the substrate and a conductive layer. The conductive layer is printed on the surface of the substrate and has the working electrode, the reference electrode and the auxiliary electrode, wherein the working electrode includes the porous carbon layer, the graphene layer and the catalyst layer. The porous carbon layer is connected to the conductive layer. The graphene layer is connected to the porous carbon layer. The catalyst layer is electroplated on the graphene layer, and the catalyst layer includes the metal oxide and is used to oxidize the analyte.

According to still another aspect of the present disclosure, a non-enzyme sensor for detecting a concentration of an analyte includes the non-enzyme sensor element according to the aforementioned aspect and a current sensor. The non-enzyme sensor element is used to oxidize the analyte to generate a current. The current sensor is electrically connected to the non-enzyme sensor element and converts the current to a concentration signal.

BRIEF DESCRIPTION OF THE DRAWINGS

The present disclosure can be more fully understood by reading the following detailed description of the embodiment, with reference made to the accompanying drawings as follows.

DETAILED DESCRIPTION

Figure 1:
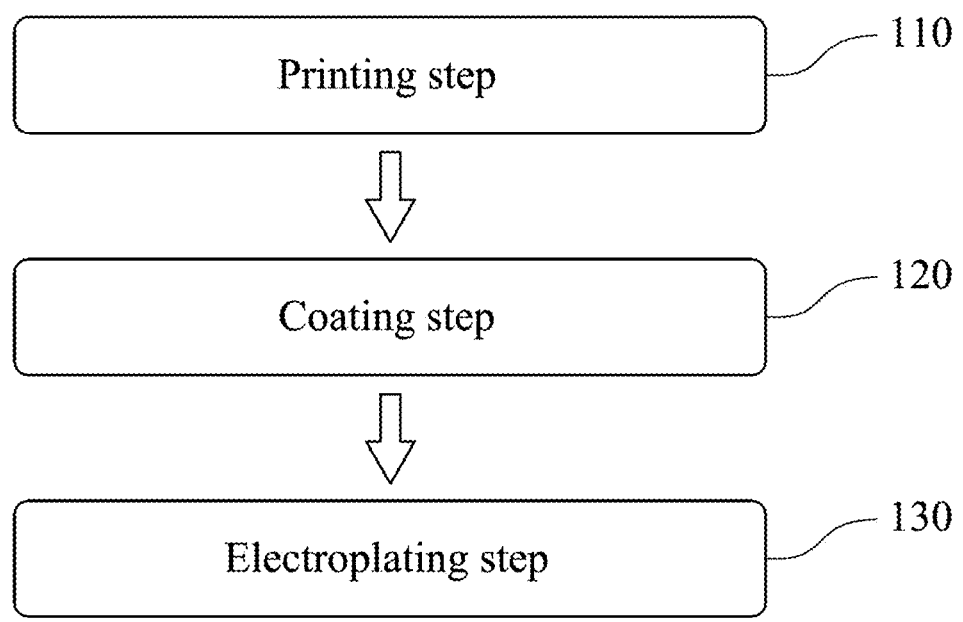
FIG. 1 is a block diagram of a fabricating method of a non-enzyme sensor element according to one embodiment of the present disclosure.
Figure 3:
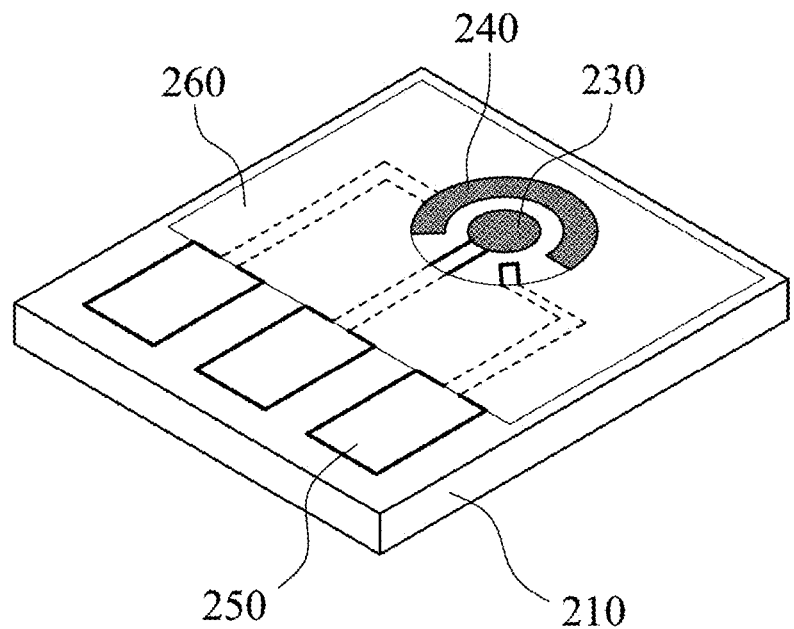
FIG. 3 is a schematic view of a non-enzyme sensor element according to still another embodiment of the present disclosure.
Figure 4:
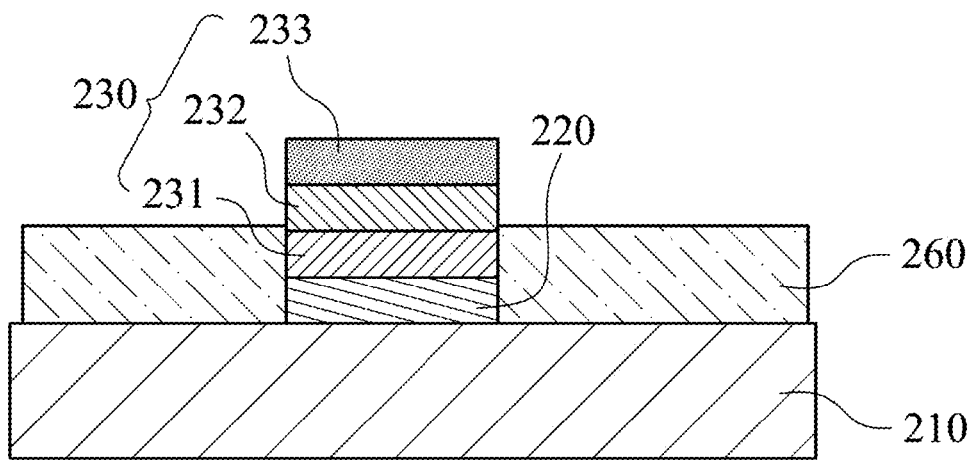
FIG. 4 is a sectional schematic view of the non-enzyme sensor element of FIG. 3.

FIG. 1 is a block diagram of a fabricating method of a non-enzyme sensor element 100 according to one embodiment of the present disclosure. FIG. 3 is a schematic view of a non-enzyme sensor element 200 according to still another embodiment of the present disclosure. FIG. 4 is a sectional schematic view of the non-enzyme sensor element 200 of FIG. 3. The non-enzyme sensor element 200 of FIGS. 3 and 4 can be fabricated by the fabricating method of the non-enzyme sensor element 100 of FIG. 1.

The non-enzyme sensor element 200 includes a substrate 210 and a conductive layer 220. The conductive layer 220 is printed on the surface of the substrate 210 and has a working electrode 230, a reference electrode 240 and an auxiliary electrode 250. As shown in FIG. 4, the working electrode 230 includes a porous carbon layer 231, a graphene layer 232 and a catalyst layer 233. The porous carbon layer 231 is connected to the conductive layer 220, the graphene layer 232 is connected to the porous carbon layer 231, the catalyst layer 233 is electroplated on the graphene layer 232, and the catalyst layer 233 is used for oxidizing the analyte and includes the metal oxide.

Figure 5:
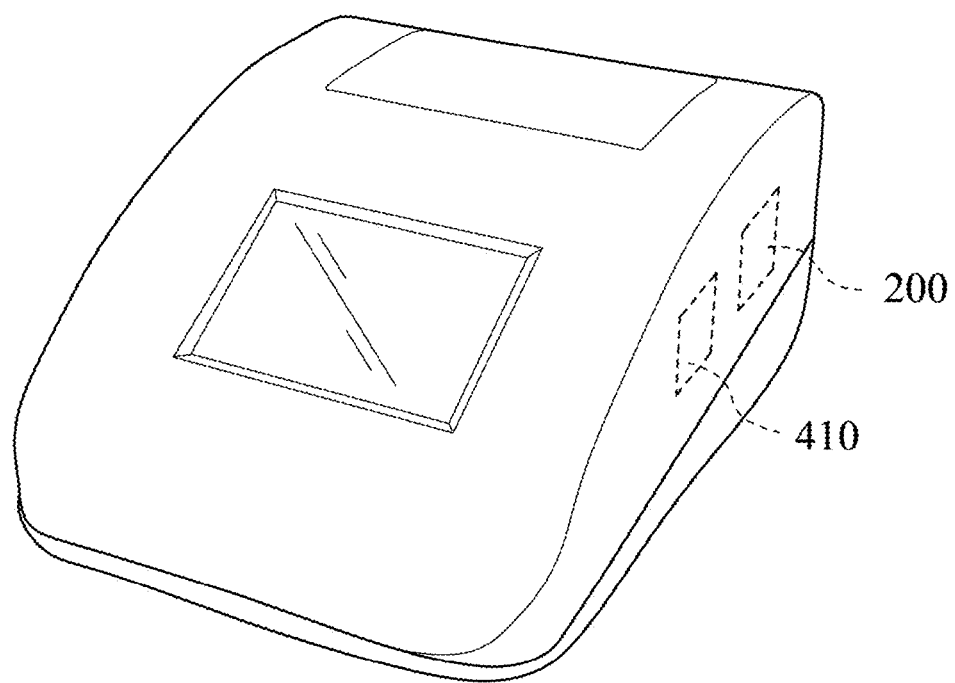
FIG. 5 is a schematic view of a non-enzyme sensor according to still another embodiment of the present disclosure.

FIG. 5 is a schematic view of a non-enzyme sensor 400 according to still another embodiment of the present disclosure. The non-enzyme sensor 400 is used for detecting a concentration of the analyte and includes the non-enzyme sensor element 200 and a current sensor 410, and the current sensor 410 is electrically connected to the non-enzyme sensor element 200. The non-enzyme sensor element 200 is for oxidizing the analyte to generate a current, and the current sensor 410 is used for detecting the current and transforming the current to a concentration signal.

The analyte can be a volatile fatty acid, a sugar or an alcohol. In detail, the volatile fatty acid can be a lactic acid, the sugar can be a glucose and the alcohol can be an ethanol, but the present disclosure will not be limited thereto. An oxidation reaction is conducted by the catalyst layer 233 of the non-enzyme sensor element 200 and the analyte. In detail, the metal oxide of the catalyst layer 233 oxidizes the analyte and generates the current, the current sensor 410 detects the current and converts the current to a concentration signal. That is, the intensity of the current can be used to determine the concentration of the analyte in the test solution. Therefore, the concentration of the analyte can be obtained accurately.

The non-enzyme sensor element 200 fabricated by the fabricating method of the non-enzyme sensor element 100 has excellent sensitivity, stability and wide detecting range. Therefore, the analyte detecting accuracy of the non-enzyme sensor 400 can be further improved, and the non-enzyme sensor 400 can be widely used in the field of the biological detection and the clinical medicine.

The fabricating method of the non-enzyme sensor element 100, the non-enzyme sensor element 200 and the non-enzyme sensor 400 will be described in detail below.

In detail, the fabricating method of the non-enzyme sensor element 100 in FIG. 1 includes a printing step 110, a coating step 120 and an electroplating step 130. In the printing step 110, a conductive material is printed on a surface of the substrate 210 to form the working electrode 230, the reference electrode 240 and the auxiliary electrode 250, and a porous carbon material is printed on the working electrode 230 to form the porous carbon layer 231. In the coating step 120, a graphene film material is coated on the porous carbon layer 231 of the working electrode 230 and to form the graphene layer 232. In the electroplating step 130, a metal is electroplated on the graphene layer 232 by a pulse constant current to form the catalyst layer 233, and the catalyst layer 233 can include a metal oxide.

In order to more clearly describe the efficacy of the fabricating method of the non-enzyme sensor element 100 according to present disclosure, the detailed steps of the fabricating method of the non-enzyme sensor element 100 will be described in detail below.

The fabricating method of the non-enzyme sensor element 100 first performs the printing step 110. In the printing step 110 of FIG. 1, the conductive material is printed on the surface of the substrate 210 by a screen with a thickness of 10 μm and a mesh size of 300 meshes to form the conductive layer 220, and then is divided into the working electrode 230, the reference electrode 240 and the auxiliary electrode 250. In the embodiment of FIG. 1, the conductive material can be silver paste, but the present disclosure will not be limited thereto.

On the other hand, in the preparation method of the reference electrode 240, a ferric chloride ($FeCl_3$) is dropped on the conductive layer 220 of the reference electrode 240 to form a silver chloride compound after the conductive layer 220 has been printed in the printing step 110, and so as to finish an electrode modification of the reference electrode 240. By the method described above, the electrode modification of the reference electrode 240 can be completed directly on the substrate 210, which is helpful to improve the manufacturing efficiency of the fabricating method of the non-enzyme sensor element 100.

After that, the porous carbon material is printed on the surface of the conductive layer 220 of the working electrode 230 to form the porous carbon layer 231. In detail, the porous carbon material is prepared by mixing carbon slurry and calcium carbonate powder and the weight percentage of the calcium carbonate powder is 40%. The porous carbon material mentioned above is printed on the surface of the conductive layer 220 of the working electrode 230, the working electrode 230 with the porous carbon material is placed in a solution with 1M HCl and quickly stirred for 1 hour to remove the calcium carbonate powder, and form a plurality of pores on the surface of the porous carbon material, then the working electrode 230 is washed with deionized water and dried naturally, and the formation of the porous carbon layer 231 on the surface of the conductive layer 220 is completed. It should be mentioned that, the material for preparing the porous carbon material can be other soluble powders, and the preparation of the porous carbon material of the porous carbon layer 231 will not be limited thereto.

The porous carbon layer 231 made by the printing step 110 has low manufacturing cost and simple operation, and the manufacturing efficiency of the fabricating method of the non-enzyme sensor element 100 of the present disclosure can be improved. Besides, the porous carbon layer 231 made by the printing step 110 has a plurality of pores on the surface. That is, the porous carbon layer 231 has a high specific surface area, which can increase the active area of the porous carbon layer 231.

Further, the wire pattern can be drawn by a drawing software such as AutoCAD before performing the printing step 110, and the conductive material can be printed according to the wire pattern to meet the application requirements of different wire patterns.

The coating step 120 is performed after the porous carbon layer 231 formed. In the coating step 120, a graphene film material is coated on the surface of the porous carbon layer 231 of the working electrode 230 and dried with a planer heater at 40° C. and to form the graphene layer 232. In detail, the graphene film material is made by mixing a graphene powder and a proton exchange membrane (such as Nafion). The graphene film material is stuck on the surface of the porous carbon layer 231 to form the graphene layer 232 via the adhesive property of the proton exchange membrane.

The method for preparing the graphene film material is to add graphene oxide powder to deionized water to form a graphene dispersion having a concentration of 0.5 g/L, and place the graphene dispersion mentioned above in ultrasonicator for a period of time. Then the proton exchange membrane solution with a weight percentage of 5% is mixed with the graphene dispersion solution in a ratio of 1:1, and placed in the ultrasonicator for one hour to form the graphene film material.

In addition, before performing the coating step 120, the porous carbon layer 231 of the working electrode 230 can be washed to increase the stability of the working electrode 230. Specifically, the porous carbon layer 231 made by the printing step 110 is placed in 1 M sulfuric acid, and the surface of the porous carbon layer 231 of the working electrode 230 is cleaned by Cyclic Voltammetry (CV) under the conditions of a scanning voltage of −1.2 V to −1.8 V, a scanning rate of 100 mV/S and a cycle number of 20. Therefore, the coating step 120 is facilitated, and the graphene film material can be coated on the surface of the porous carbon layer 231 uniformly.

Next, in the electroplating step 130, an electroplating solution is prepared by mixing a 40 mM metal nitrate compound, a sulfuric acid and a boric acid, and adjusting the electroplating solution to pH 2. The electroplating solution and the working electrode 230 are placed in an electroplating bath to perform the chemical deposition to the graphene layer 232 of the working electrode 230 with the pulse constant current. The metal ions in the electroplating solution are electroplated on the surface of the graphene layer 232 to form the catalyst layer 233. In detail, in the electroplating step 130, the metal deposited on the surface of the graphene layer 232 is oxidized on the surface of the graphene layer 232 to form a metal oxide which can be regarded as a catalyst with strong oxidation-reduction capability.

In FIG. 1, the current density of the pulse constant current can be −0.8 A/ft$^2$, and the first period of the pulse constant current can be 3 seconds, the second period can be 2.5 seconds, and the number of cycles can be 300. Compared to the general plating method, a more uniform and dense catalyst layer 233 can be formed on the surface of the working electrode 230 by electroplated with the pulse constant current. Therefore, the oxidation-reduction capability of the catalyst layer 233 can be increase, and the sensitivity and accuracy of the non-enzyme sensor element 200 can be also increased.

The metal provided in the electroplating step 130 can be a transition metal, such as copper or nickel, but the present disclosure will not be limited thereto. In FIG. 1, the metal provided in the electroplating step 130 is nickel. That is, the nitrate-metal compound can be nickel nitrate, and the catalyst layer 233 of the non-enzyme sensor element 200 can include nickel oxide, but the present disclosure will not be limited thereto, the metal mentioned above can also be cobalt or copper, which can be selected according to the application requirements.

It should be mentioned that, the experimental parameters and preparation materials in the fabricating method of the non-enzyme sensor element 100 will not be limited thereto, which can be adjusted according to the application requirements.

Further, the manufacturing cost of the electroplating solution prepared in the electroplating step 130 is low and the preparation method thereof is simple. In the electroplating step 130 of the fabricating method of the non-enzyme sensor element 100, the catalyst layer 233 with a nano-level catalyst can be formed by the electroplating method with the pulse constant current under conditions of low cost and simple operation. Therefore, it is beneficial to increase the manufacturing efficiency of the fabricating method of the non-enzyme sensor element 100 and achieve the goal of mass production.

The fabricating method of the non-enzyme sensor element 100 of FIG. 1 is simple, rapid and high reproducibility. Therefore, the manufacturing time and cost of the non-enzyme sensor element 200 can be effectively reduced, and it is beneficial to achieve the commodification and the mass production thereof. Further, in the fabricating method of the non-enzyme sensor element 100, the metal is electroplated on the working electrode 230 by using the pulse constant current, which can make the structure of the catalyst layer 233 denser and more uniform. Therefore, the sensitivity of the non-enzyme sensor element 200 can be increase, and the detecting range and the detecting accuracy of the non-enzyme sensor 400 can be also increased.

Figure 6:
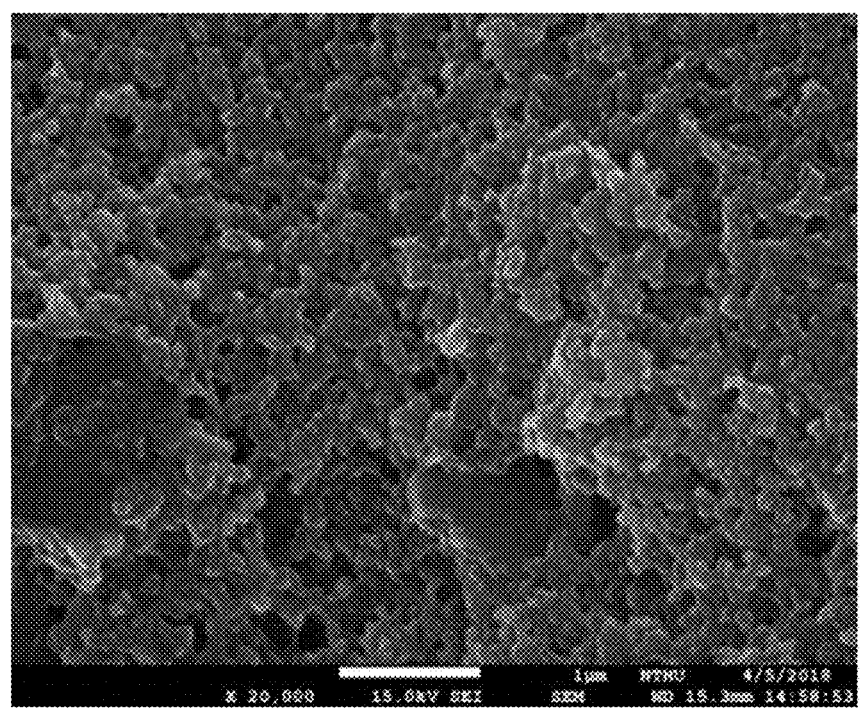
FIG. 6 is a SEM image of the porous carbon layer of the non-enzyme sensor element of FIG. 3.

FIG. 6 is a SEM image of the porous carbon layer 231 of the non-enzyme sensor element 200 of FIG. 3, and please refer to FIGS. 3 and 4 again. As shown in FIG. 4, the porous carbon layer 231 of the working electrode 230 can be disposed on the conductive layer 220, and as mentioned above, the porous carbon layer 231 with dense surface can be formed by the fabricating method of the non-enzyme sensor element 100. As shown in the SEM image of the porous carbon layer 231 of FIG. 6, the porous carbon layer 231 has a plurality of pores, and the pores can be smaller than 10 μm. Therefore, the reaction area, the oxidation-reduction capability and reaction current can be increased, which is beneficial to increase the sensitivity and concentration detecting range of the non-enzyme sensor element 200.

As shown in FIG. 4, the graphene layer 232 is disposed on the porous carbon layer 231, and as mentioned above, the graphene layer 232 is made by mixing the graphene powder and the proton exchange membrane. The graphene layer 232 can be coated uniformly on the porous carbon layer 231 with the excellent dispersibility and binding effect of the proton exchange membrane, and through the characteristics of the graphene powder, such as high specific surface and excellent electric conductivity, the sensitivity and concentration detecting range of the non-enzyme sensor element 200 can be further increased.

Further, the catalyst layer 233 of the non-enzyme sensor element 200 fabricated by the fabricating method of the non-enzyme sensor element 100 can include the metal oxide, and the metal oxide can be a nickel oxide. The nickel oxide has excellent oxidation-reduction capability and can be used as an excellent catalyst for effectively and quickly oxidizing the analyte.

Moreover, the non-enzyme sensor element 200 can detect the concentration of the analyte in a basic environment. Therefore, the redox reaction between the non-enzyme sensor element 200 and the analyte can be more stable, and the stability of the non-enzyme sensor 400 can be increased.

In FIG. 3, the non-enzyme sensor element 200 is a three-electrode system. The accuracy and stability of the non-enzyme sensor element 200 can be increased by the arrangement of the reference electrode 240 and the auxiliary electrode 250. The non-enzyme sensor element 200 can further include an insulating layer 260 covering on the working electrode 230, the reference electrode 240 and the auxiliary electrode 250. In detail, the insulating layer 260 covers the wires of the electrodes to prevent the wires of the electrodes from being exposed, therefore, the service life of the non-enzyme sensor element 200 can be increased.

On the other hand, the conductive layer 220 can include silver, and the reference electrode 240 can include a silver chloride. Silver has extremely high stability to biological field, so that the non-enzyme sensor element 200 can be widely used in the field of biomedical materials. The substrate 210 can be a flexible polymer, such as Polyimide (PI), to provide the flexibility of the non-enzyme sensor element 200. Therefore, the non-enzyme sensor element 200 can be applied in various detecting environments, and the practicality thereof can be increased, but the present disclosure will not be limited thereto.

Not only the contact area of the reaction current and the rate of the redox reaction of the analyte can be increased but also the detecting time of the non-enzyme sensor 400 can be reduced by the arrangement of the porous carbon layer 231, the graphene layer 232 and the catalyst layer 233 of the non-enzyme sensor element 200. Specifically, the time for detecting the concentration of the lactic acid of the non-enzyme sensor 400 can be 30 seconds to 45 seconds. Compared with the conventional sensor, the detecting time of the non-enzyme sensor 400 of present disclosure can be greatly reduced and so as to meet the needs of practical applications.

Figure 7:
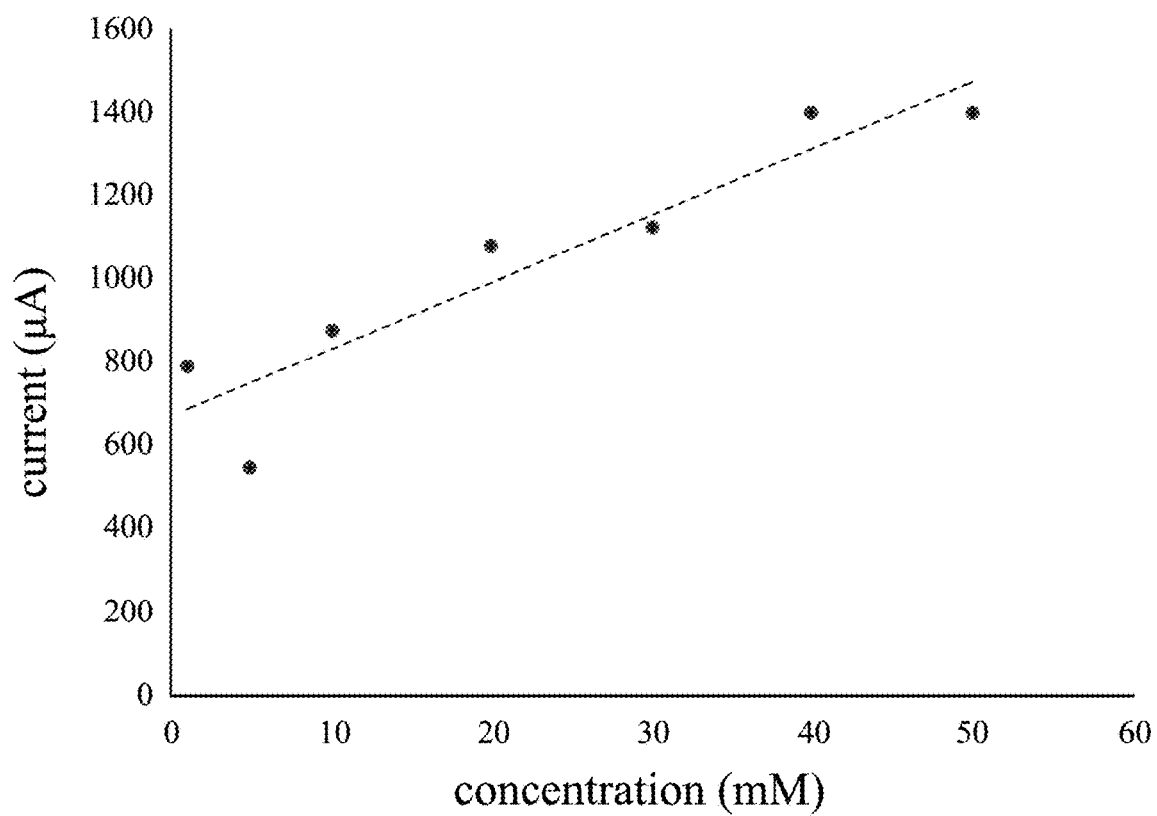
FIG. 7 is a graph of current-vs.-concentration for the lactic acid detected by the non-enzyme sensor of Example 1 according to still another embodiment in FIG. 5.

FIG. 7 is a graph of current-vs.-concentration for the lactic acid detected by the non-enzyme sensor 400 of Example 1 according to still another embodiment in FIG. 5. Table 1 describes the detecting data of the lactic acid detected by the non-enzyme sensor 400. The non-enzyme sensor 400 of Example 1 includes the non-enzyme sensor element 200 described above, and the catalyst layer 233 of the non-enzyme sensor element 200 can include the nickel oxide. In FIG. 7, the linear function $R^2$ of the non-enzyme sensor 400 of Example 1 is 0.8703 in the linear range of 1 mM to 50 mM, which shows that it has excellent stability and accuracy.

The conventional non-enzyme sensor detects the lactic acid concentration in two ranges of 0.5 mM to 35 mM and 11.9 mM to 188 mM. However, the range of the lactic acid concentration in the human body fluid can be as wide as 0 mM to 60 mM. It shows that each conventional non-enzyme sensor alone is not suitable for human metabolites detection. The concentration detecting range of the lactic acid of the non-enzyme sensor 400 can cover the range of the lactic acid of the human body. Therefore, the non-enzyme sensor 400 and the non-enzyme sensor element 200 can be widely used in the field of human medical detection, and the problem of incomplete range of the conventional non-enzyme sensor can be solved.

TABLE 1

| Concentration (mM) | Current (μA) |
|---|---|
| 1 | 789.7021 |
| 5 | 543.4833 |
| 10 | 872.7029 |
| 20 | 1080.24 |
| 30 | 1122.321 |
| 40 | 1403.854 |
| 50 | 1396.138 |

Figure 2:
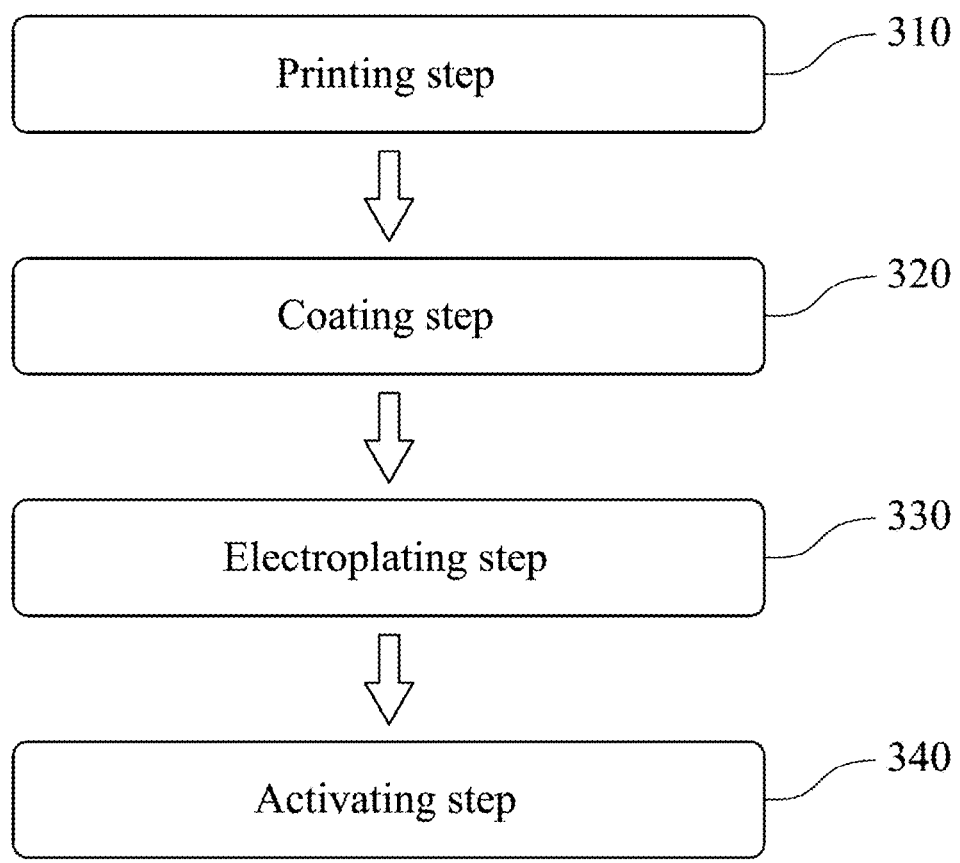
FIG. 2 is a block diagram of the fabricating method of a non-enzyme sensor element according to another embodiment of the present disclosure.

The catalyst layer 233 of the non-enzyme sensor element 200 can further include a metal hydroxide in order to increase the detecting effect of the non-enzyme sensor element 200. FIG. 2 is a block diagram of a fabricating method of non-enzyme sensor element 300 according to another embodiment of the present disclosure. The fabricating method of the non-enzyme sensor element 300 includes a printing step 310, a coating step 320, an electroplating step 330 and an activating step 340, wherein the printing step 310, the coating step 320 and the electroplating step 330 are the same as the printing step 110, the coating step 120 and the electroplating step 130 in FIG. 1, and detailed steps will not be described here again. The difference between the fabricating method of the non-enzyme sensor element 300 of FIG. 2 and the fabricating method of the non-enzyme sensor element 100 of FIG. 1 is that the fabricating method of the non-enzyme sensor element 300 of FIG. 2 further includes the activating step 340. In the activating step 340, the metal oxide is transformed to a metal hydroxide so as to further increase the oxidation-reduction capability of the catalyst layer 233.

In detail, in the activating step 340, the metal oxide of the catalyst layer 233 is transformed to the metal hydroxide by Cyclic Voltammetry in a 1M sodium hydroxide solution and under the conditions of the scanning voltage of 0 V to 0.7 V, the scanning rate of 50 mV/S and the cycle number of 50. The catalyst layer 233 fabricated by the activating step 340 uses the metal hydroxide with the strong oxidation-reduction capability as the catalyst for reacting with the analyte. Therefore, the sensitivity, the accuracy and the concentration detecting range of the non-enzyme sensor element 200 can be increased. It is specifically stated that the experimental parameters mentioned above can be adjusted according to application requirements, and the present disclosure will not be limited thereto.

After the activating step 340, the nickel oxide of the catalyst layer 233 of the non-enzyme sensor element 200 is transformed into nickel hydroxide, and the chemical equation of the activating step 340 is shown as follow:

$$Ni+2OH^- \rightarrow \beta\text{-}Ni(OH)_2+e^- \qquad \text{equation (1)}.$$

Specifically, the non-enzyme sensor element 200 can detect the concentration of an analyte in a basic environment. The nickel hydroxide ($Ni(OH)_2$) is transformed into the nickel oxide hydroxide (NiOOH) in the basic environment which can be regarded as a strong oxidant. Next, the lactic acid can be oxidized to the pyruvic acid by the nickel oxide hydroxide, and a current can be generated in the redox reaction. The current generated by nickel oxide hydroxide oxidizing the lactic acid is received by the current sensor 410, and the current sensor 410 converts the current to a concentration signal so as to obtain the concentration of the lactic acid in the detected solution. The chemical equation for detecting the lactic acid are shown as follow:

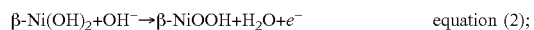
$$\beta\text{-}Ni(OH)_2+OH^- \rightarrow \beta\text{-}NiOOH+H_2O+e^- \qquad \text{equation (2)};$$

$$\beta\text{-}NiOOH+\text{Lactic acid}+e^- \rightarrow \beta\text{-}Ni(OH)_2+\text{Pyruvic acid} \qquad \text{equation (3)}.$$

It is worth mentioning that, as known in the chemical equation mentioned above, the nickel hydroxide as an oxidation reaction catalyst can be regenerated. Therefore, the non-enzyme sensor element 200 of present disclosure can be reused, and the practicality thereof can be increased.

Figure 8:
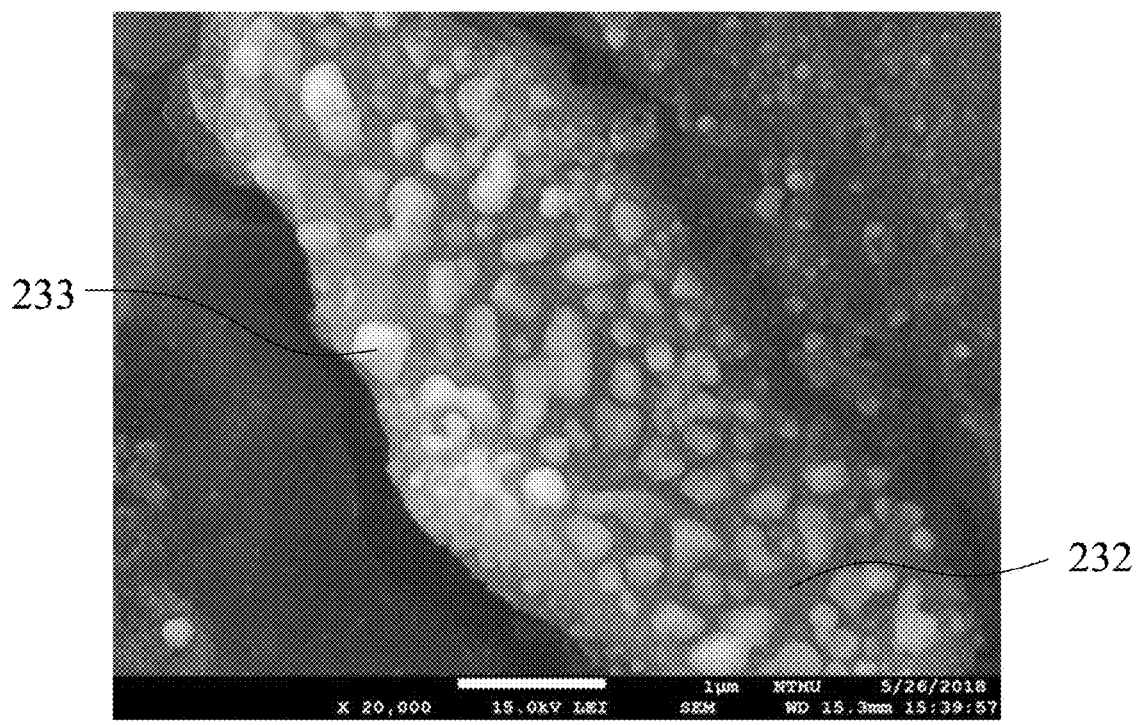
FIG. 8 is a SEM image of the catalyst layer of the non-enzyme sensor element of FIG. 3.
Figure 9:
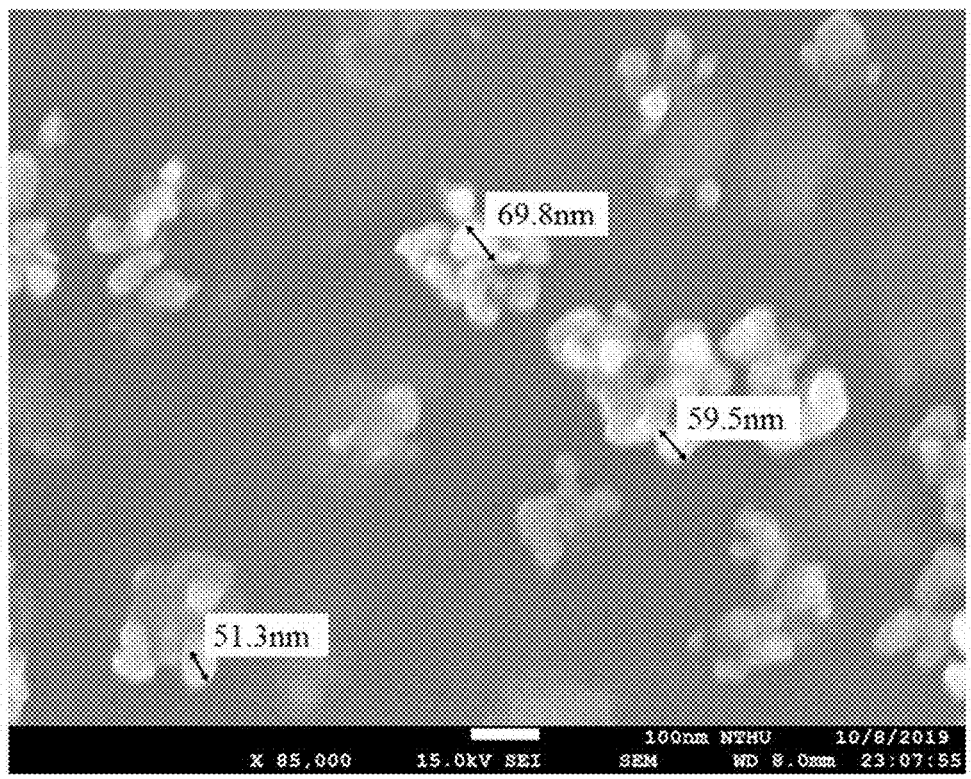
FIG. 9 is another SEM image of the catalyst layer of the non-enzyme sensor element of FIG. 3.

FIG. 8 is a SEM image of the catalyst layer 233 of the non-enzyme sensor element 200 of FIG. 3. FIG. 9 is another SEM image of the catalyst layer 233 of the non-enzyme sensor element 200 of FIG. 3. The catalyst layer 233 in FIGS. 8 and 9 is fabricated by the activating step 340. In FIG. 8, the catalyst layer 233 including the nickel hydroxide uniformly electroplated on the graphene layer 232. The particles shown in FIG. 9 are the nickel hydroxide, as shown in FIG. 9, the nickel hydroxide are agglomerated on the graphene layer 232, and the size of the particles of the nickel hydroxide can be 50 nm to 90 nm. The reaction area and the reaction current can be increased by the nano-level nickel hydroxide on the catalyst layer 233, and the sensitivity and the accuracy of the non-enzyme sensor element 200 can be further increased.

Figure 10:
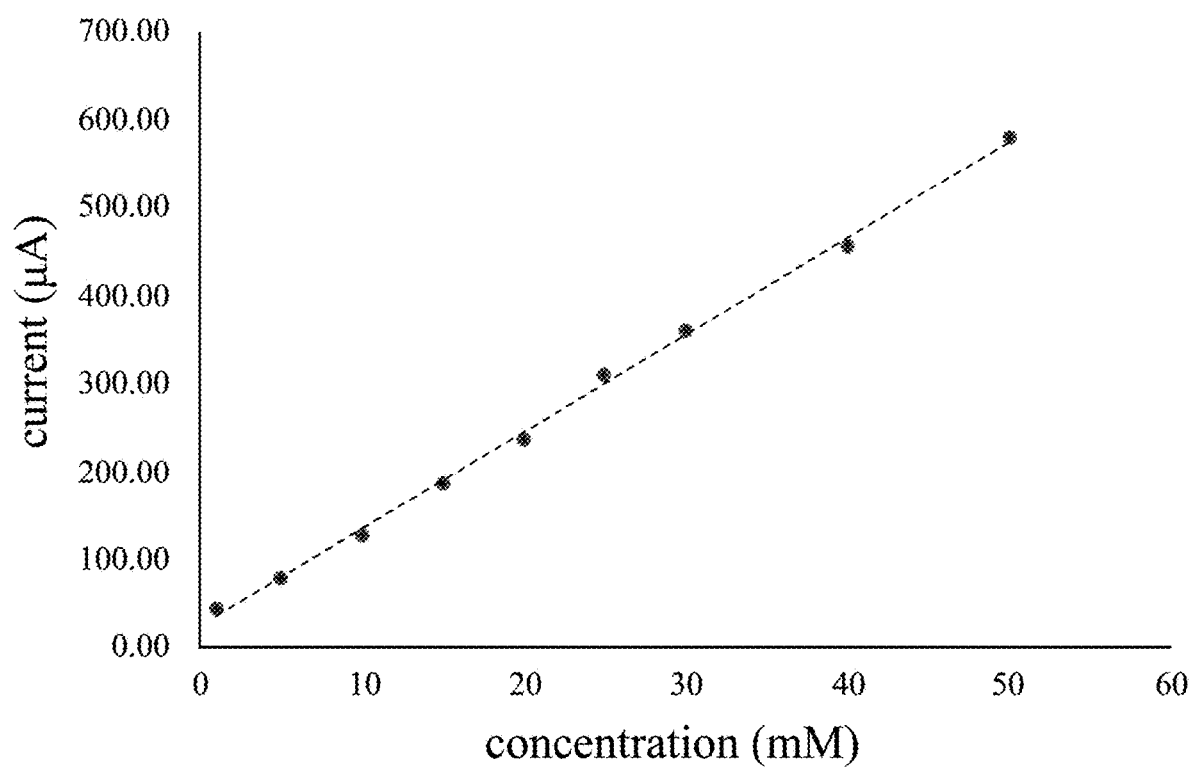
FIG. 10 is a graph of current-vs.-concentration for the lactic acid detected by the non-enzyme sensor of Example 2 according to still another embodiment in FIG. 5.

FIG. 10 is a graph of current-vs.-concentration for the lactic acid detected by the non-enzyme sensor 400 of Example 2 according to still another embodiment in FIG. 5. Table 2 describes the detecting data of the lactic acid detected by the non-enzyme sensor 400. The non-enzyme sensor element 200 of the non-enzyme sensor 400 of Example 2 is fabricated by the fabricating method of the non-enzyme sensor element 400 of FIG. 3, that is, the non-enzyme sensor element 200 of Example 2 includes the nickel hydroxide.

Specifically, the experimental data in FIG. 10 and Table 2 are the average values of repeated tests, and the standard error thereof is 8.94%. After calculating the data of the FIG. 10 and Table 2, it can be known that the average sensitivity is 11.74±1.05 μA/mM and the linear function $R^2$ is 0.998. It shows that the non-enzyme sensor 400 has excellent detecting sensitivity and accuracy for detecting the concentration of the lactic acid through the non-enzyme sensor element 200.

TABLE 2

| Concentration (mM) | Current (μA) |
| --- | --- |
| 1 | 39.16 |
| 5 | 69.00 |
| 10 | 121.49 |
| 15 | 182.16 |
| 20 | 238.39 |
| 25 | 329.18 |
| 30 | 347.64 |
| 40 | 476.22 |
| 50 | 582.36 |

Further, the concentration detecting range of the lactic acid of the non-enzyme sensor 400 can be 1 mM to 50 mM. In FIG. 10, the non-enzyme sensor 400 has excellent stability and accuracy in the linear range of 1 mM to 50 mM. Therefore, the problem of incomplete range and low accuracy of the conventional non-enzyme sensor can be solved.

Figure 11:
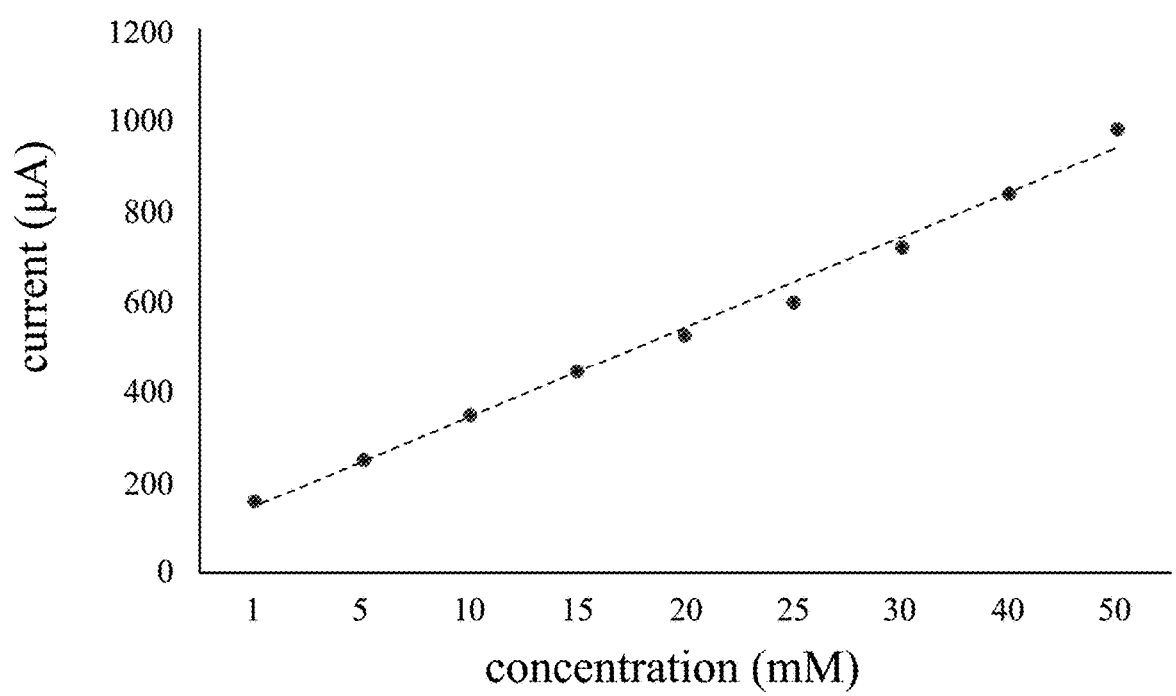
FIG. 11 is a graph of current-vs.-concentration for the glucose detected by the non-enzyme sensor of Example 2 according to still another embodiment in FIG. 5.

FIG. 11 is a graph of current-vs.-concentration for the glucose detected by the non-enzyme sensor 400 of Example 2 according to still another embodiment in FIG. 5. Table 3 describes the detecting data of the glucose detected by the non-enzyme sensor 400. Specifically, the experimental data in FIG. 11 and Table 3 are the average values of repeated tests, and the standard error thereof is 25.13%. After calculating the data of the FIG. 11 and Table 3, the average sensitivity is 15.6±3.92 μA/mM, the linear range is 1 mM to 20 mM, and the linear function $R^2$ is 0.9924 when the non-enzyme sensor 400 is used to detect the concentration of the glucose. It shows that the non-enzyme sensor element 200 has excellent detecting sensitivity and accuracy for detecting the concentration of the glucose. Therefore, the non-enzyme sensor 400 can detect the concentration of the glucose more accurately.

TABLE 3

| Concentration (mM) | Current (μA) |
| --- | --- |
| 1 | 162.45 |
| 5 | 254.25 |
| 10 | 352.56 |
| 15 | 451.78 |
| 20 | 530.94 |
| 25 | 604.09 |
| 30 | 723.81 |
| 40 | 945.15 |
| 50 | 986.91 |

Figure 12:
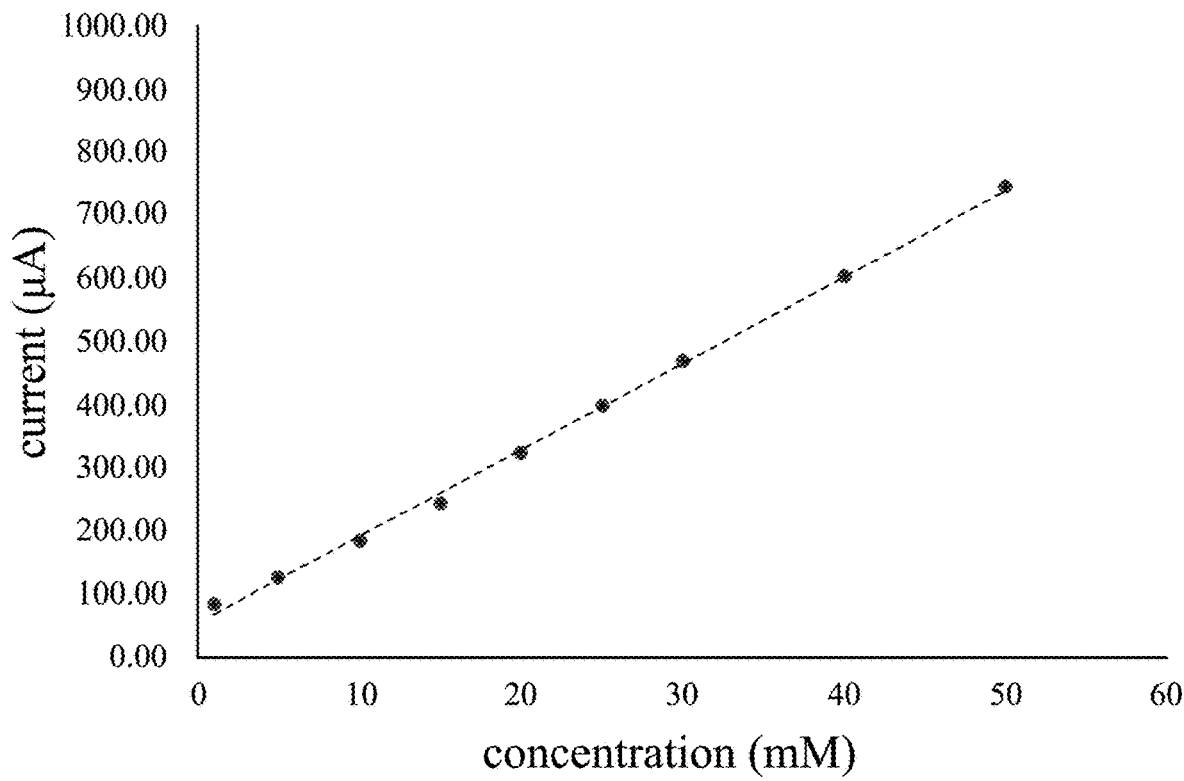
FIG. 12 is a graph of current-vs.-concentration for the ethanol detected by the non-enzyme sensor of Example 2 according to still another embodiment in FIG. 5.

FIG. 12 is a graph of current-vs.-concentration for the ethanol detected by the non-enzyme sensor 400 of Example 2 according to still another embodiment in FIG. 5. Table 4 describes the detecting data of the ethanol detected by the non-enzyme sensor 400. Specifically, the experimental data in FIG. 12 and Table 4 are the average values of repeated tests, and the standard error thereof is 13.43%. After calculating the data of the FIG. 12 and Table 4, it shows that, the average sensitivity is 13.70±1.84 μA/mM, the linear range is 1 mM to 50 mM, and the linear function $R^2$ is 0.998 when the non-enzyme sensor 400 is used to detect the concentration of the ethanol. It shows that he non-enzyme sensor element 200 has excellent detecting sensitivity and accuracy for detecting the concentration of the ethanol. Therefore, the non-enzyme sensor 400 can detect the concentration of the ethanol more accurately.

TABLE 4

| Concentration (mM) | Current (μA) |
| --- | --- |
| 1 | 94.51 |
| 5 | 136.84 |
| 10 | 201.56 |
| 15 | 256.09 |
| 20 | 323.81 |
| 25 | 388.72 |
| 30 | 452.05 |
| 40 | 554.72 |
| 50 | 733.52 |

In order to illustrate the advantages of the non-enzyme sensor element 200 fabricated by the fabricating method of the non-enzyme sensor element 300, the non-enzyme sensors of Comparative Example 1 and Comparative Example 2 are compared with the non-enzyme sensor 400 of Example 2 described above, and the effects of detecting the concentration of the lactic acid thereof are compared and analyzed. The results of the analysis will be detailed below.

In order to more clearly illustrate the effect of the porous carbon layer 231 of the non-enzyme sensor element 200 of present disclosure, the difference between Comparative Example 1 and Example 2 is that the working electrode of Comparative Example 1 is conventional Au substrate; and the difference between Comparative Example 2 and Example 2 is that the working electrode of Comparative Example 2 is conventional carbon substrate.

Figure 13:
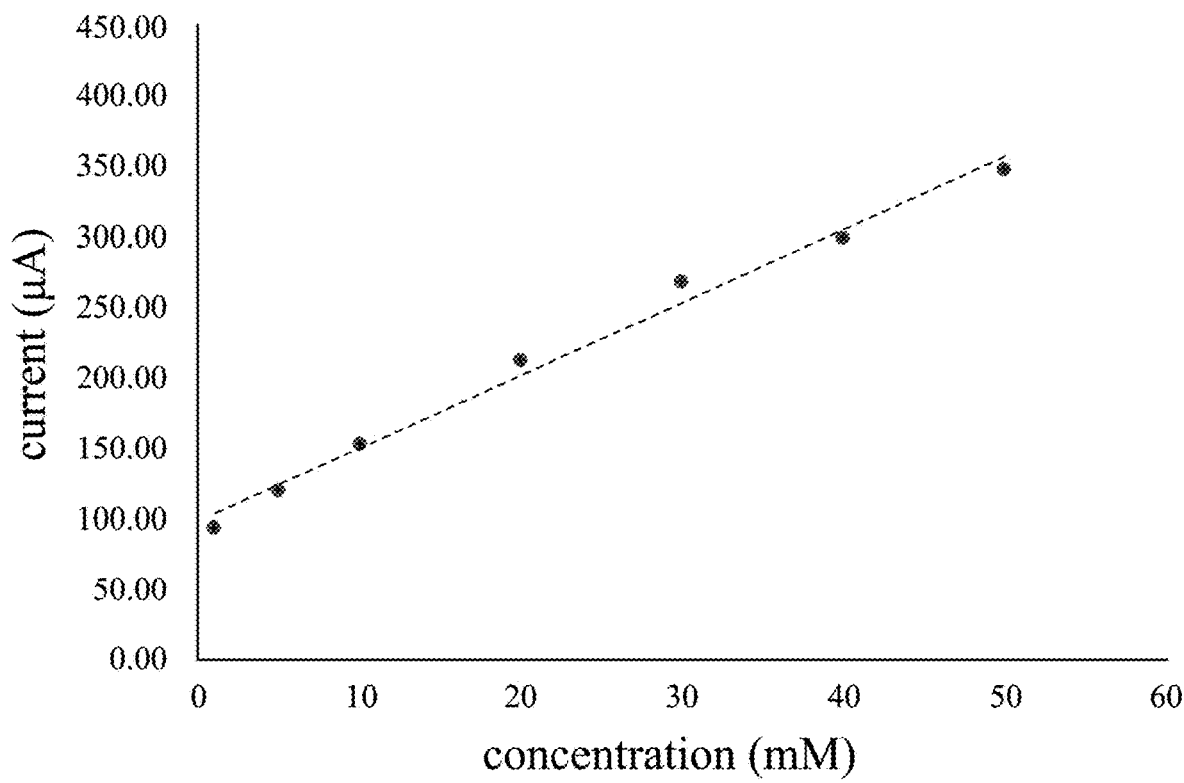
FIG. 13 is another graph of current-vs.-concentration for the lactic acid detected by the non-enzyme sensor of Example 2 according to still another embodiment in FIG. 5.

FIG. 13 is another graph of current-vs.-concentration for the lactic acid detected by the non-enzyme sensor 400 of Example 2 according to still another embodiment in FIG. 5. Table 5 describes the detecting data in the concentration range of 1 mM to 50 mM of the lactic acid detected by the non-enzyme sensor 400. After calculating the detecting data of FIG. 13 and Table 5, the linear function $R^2$ of Example 2 is 0.9899, showing that the non-enzyme sensor 400 of Example 2 can detect the concentration of the lactic acid accurately.

TABLE 5

| Concentration (mM) | Current (µA) |
| --- | --- |
| 1 | 93.44533 |
| 5 | 120.3479 |
| 10 | 153.1642 |
| 20 | 212.3033 |
| 30 | 267.8992 |
| 40 | 299.2988 |
| 50 | 347.9908 |

Figure 14:
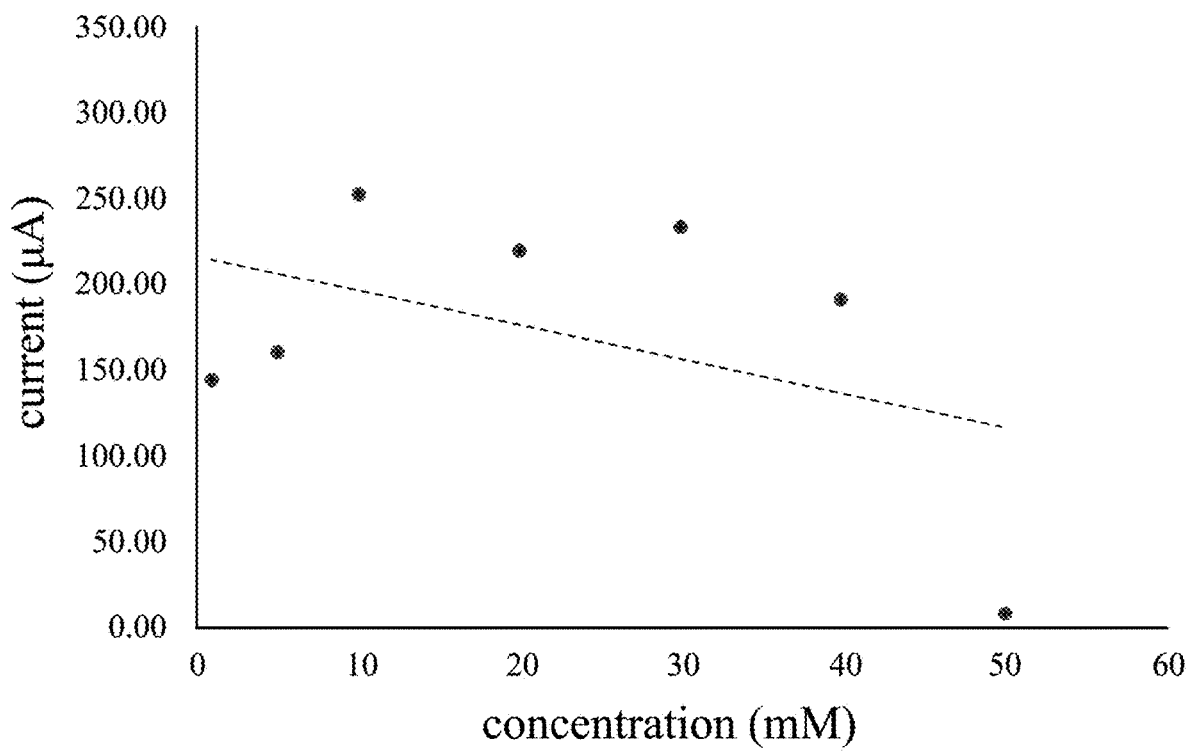
FIG. 14 is a graph of current-vs.-concentration for the lactic acid detected by the non-enzyme sensor of Comparative Example 1.

Please refer to FIG. 14 and Table 6, and also refer to FIG. 13 and Table 5. FIG. 14 is a graph of current-vs.-concentration for the lactic acid detected by the non-enzyme sensor of Comparative Example 1. Table 6 describes the detecting data in the concentration range of 1 mM to 50 mM of the lactic acid detected by Comparative Example 1.

As shown in FIGS. 13 and 14 and the detecting data of Example 2 and Comparative Example 1, the linear performance of Example 2 is significantly more stable than the linear performance of Comparative Example 1. After calculating the detecting data of Table 6, the linear function $R^2$ of Comparative Example 1 is 0.1973, which compared to the linear function $R^2$ of Example 2 is 0.9899, it shows that the sensitivity and the accuracy of the non-enzyme sensor 400 can be increased by the porous carbon layer 231 of Example 2. Therefore, the problem of low accuracy of the working electrode with the Au substrate of the conventional non-enzyme sensor can be improved.

TABLE 6

| Concentration (mM) | Current (µA) |
| --- | --- |
| 1 | 144 |
| 5 | 161 |
| 10 | 251 |
| 20 | 219 |
| 30 | 232 |
| 40 | 191 |
| 50 | 7.18 |

Figure 15:
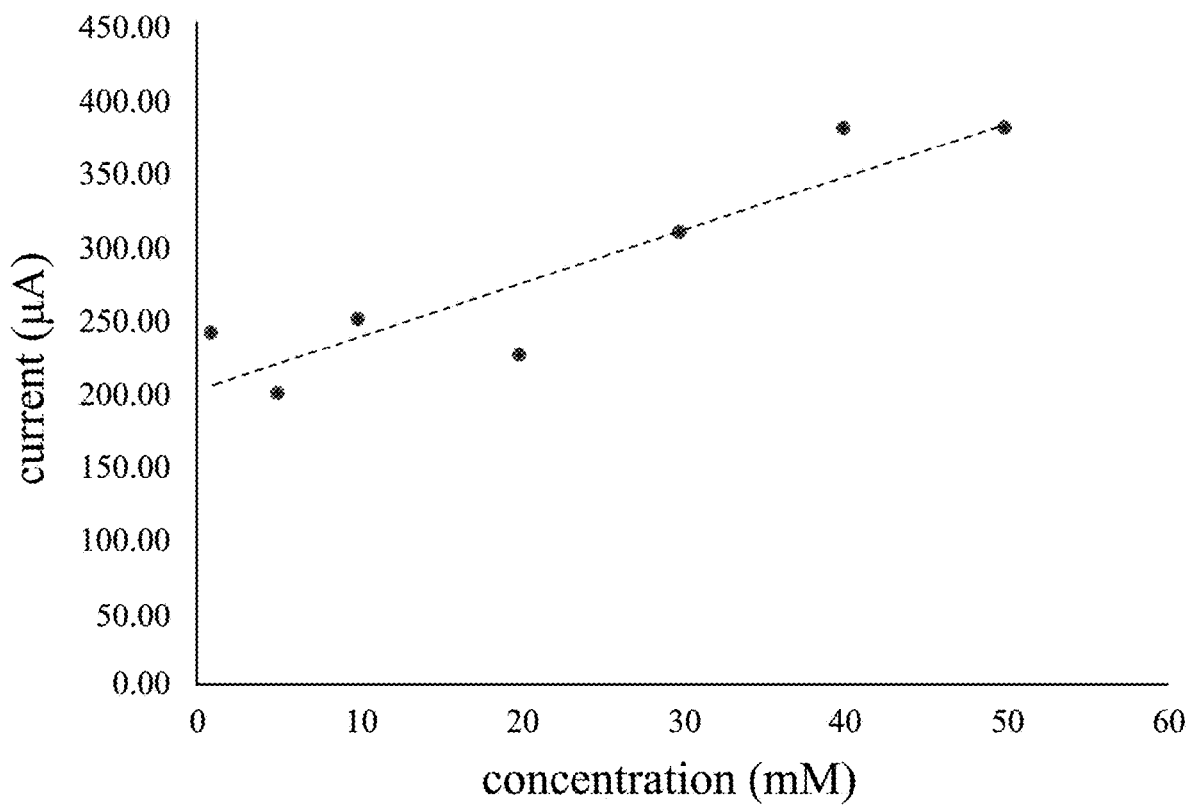
FIG. 15 is a graph of current-vs.-concentration for the lactic acid detected by the non-enzyme sensor of Comparative Example 2.

Please refer to FIG. 15 and Table 7, and also refer to FIG. 13 and Table 5. FIG. 15 is a graph of current-vs.-concentration for the lactic acid detected by the non-enzyme sensor of Comparative Example 2. Table 7 describes the detecting data in the concentration range of 1 mM to 50 mM of the lactic acid detected by Comparative Example 1.

As shown in FIGS. 13 and 15, the linear performance of Example 2 is significantly more stable than the linear performance of Comparative Example 2. After calculating the detecting data of Table 7, the linear function $R^2$ of Comparative Example 2 is 0.8402. Showing that the detecting data of Example 2 has better linear function in the concentration detecting range of the lactic acid of 1 mM to 50 mM. It shows that the sensitivity and the accuracy of the non-enzyme sensor 400 can be increased by the porous carbon layer 231, and the accuracy thereof is better than the conventional carbon substrate.

TABLE 7

| Concentration (mM) | Current (µA) |
| --- | --- |
| 1 | 238.10 |
| 5 | 198.35 |
| 10 | 248.18 |
| 20 | 223.69 |
| 30 | 306.90 |
| 40 | 377.10 |
| 50 | 377.37 |

In summary, the non-enzyme sensor element with the excellent sensitivity can be fabricated by the fabricating method of the non-enzyme sensor element of present disclosure. Therefore, the detecting range and the accuracy can be increased, and the time for detecting can be induced so as to increase the detecting efficiency of the non-enzyme sensor. Therefore, the non-enzyme sensor of present disclosure can be widely used in the fields of clinical medicine and human medical detection.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. A fabricating method of a non-enzyme sensor element, comprising:
   a printing step, wherein a conductive material is printed on a surface of a substrate to form a working electrode, a reference electrode and an auxiliary electrode, and a porous carbon material is printed on the working electrode to form a porous carbon layer;
   a coating step, wherein a graphene film material is coated on the porous carbon layer of the working electrode to form a graphene layer; and
   an electroplating step, wherein an electroplating solution is prepared and used to electroplate a metal on the graphene layer by a pulse constant current to form a catalyst layer including a metal oxide, and
   wherein the electroplating solution is used to oxidize the electroplated metal to form the metal oxide of the catalyst layer.

2. The fabricating method of the non-enzyme sensor element of claim 1, further comprising an activating step, wherein the metal oxide is transformed to a metal hydroxide in the activating step.

3. The fabricating method of the non-enzyme sensor element of claim 1, wherein the metal provided in the electroplating step is a transition metal.

4. The fabricating method of the non-enzyme sensor element of claim 3, wherein the transition metal is nickel.

5. The fabricating method of the non-enzyme sensor element of claim 1, wherein the electroplating solution includes a nitrate-metal compound, a sulfuric acid and a boric acid.

* * * * *